(12) United States Patent
Pearlman et al.

(10) Patent No.: US 6,828,120 B2
(45) Date of Patent: Dec. 7, 2004

(54) PROCESS TO PREPARE 11β, 17α,21-TRIHYDROXY-6α-METHYLPREGNA-1,4-DIENE-3,20-DIONE 21-ACETATE

(75) Inventors: Bruce Allen Pearlman, Kalamazoo, MI (US); Michael J. White, Portage, MI (US); Ivan G. Gilbert, Kalamazoo, MI (US)

(73) Assignee: Pharmacia and Upjohn Company, Kalamazoo, MI (US)

( * ) Notice: Subject to any disclaimer, the term of this patent is extended or adjusted under 35 U.S.C. 154(b) by 179 days.

(21) Appl. No.: 10/172,479

(22) Filed: Jun. 14, 2002

(65) Prior Publication Data
US 2003/0044885 A1 Mar. 6, 2003

Related U.S. Application Data

(60) Provisional application No. 60/299,005, filed on Jun. 18, 2001.

(51) Int. Cl.[7] .......................... C12P 33/00; C12P 33/06; C12P 33/08; C12P 33/16; C12P 33/18
(52) U.S. Cl. ........................... 435/56; 435/52; 435/55; 435/58; 435/59; 435/61
(58) Field of Search .............................. 435/52, 55, 56, 435/58, 59, 61

(56) References Cited

U.S. PATENT DOCUMENTS

| | | | |
|---|---|---|---|
| 3,419,470 A | 12/1968 | Zaffaroni et al. | 195/51 |
| 3,530,038 A | 9/1970 | de Flines et al. | 195/51 |
| 4,353,985 A | 10/1982 | Petzoldt et al. | 435/59 |
| 4,588,683 A | 5/1986 | Goodhue et al. | 435/59 |
| 4,684,610 A | 8/1987 | Evans | 435/61 |
| 4,749,649 A | 6/1988 | Evans et al. | 435/61 |
| 4,898,693 A | 2/1990 | Hempel et al. | 260/397 |

FOREIGN PATENT DOCUMENTS

| | | |
|---|---|---|
| GB | 2318790 | 5/1998 |
| JP | 62-118898 | 5/1987 |

OTHER PUBLICATIONS

*Biotechnology and Bioengineering*, 37, 97–102 (1991).
Japanese Published Application 62-118898 May 1989.

*Primary Examiner*—Herbert J. Lilling
(74) *Attorney, Agent, or Firm*—John H. Engelmann; Bruce Stein

(57) ABSTRACT

The present invention is a novel process for the transformation of 17α-hydroxy-6α-methylpregn-4-ene-3,20-dione 17-acetate (I)

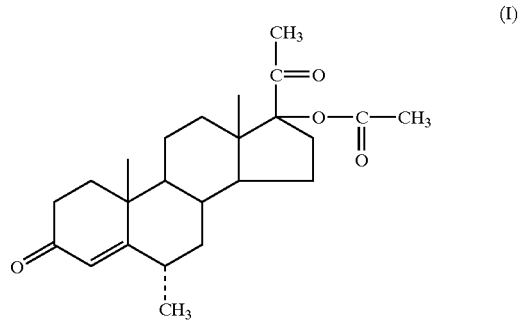

to 11β,17α,21-trihydroxy-6α-methylpregna-1,4-diene-3,20-dione 21-acetate (VI)

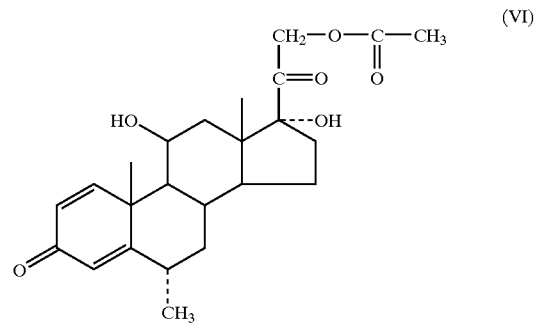

36 Claims, No Drawings

PROCESS TO PREPARE 11β, 17α,21-TRIHYDROXY-6α-METHYLPREGNA-1,4-DIENE-3,20-DIONE 21-ACETATE

CROSS-REFERENCE TO RELATED APPLICATIONS

This application claims the benefit of the following provisional application: U.S. Ser. No. 60/299,005, filed Jun. 18, 2001, under 35 USC 119(e)(i).

BACKGROUND OF THE INVENTION

1. Field of the Invention

The present invention is a process to transform medroxyprogesterone acetate (I) to 11β,17α,21-trihydroxy-6α-methylpregna-1,4-diene-3,20-dione 21-acetate (VI).

2. Description of the Related Art

The microbial enzymatic $\Delta^1$-dehydrogenation of steroids is known to those skilled in the art. *Biotechnology and Bioengineering*, 37, 97–102 (1991) discloses the $\Delta^1$-dehydrogenation of 6α-methylhydrocortisone 21-acetate by *Arthrobacter simplex* in an organic solvent.

U.S. Pat. No. 4,684,610 discloses a process for converting 1,2-saturated steroids to 1,2-dehydro, steroids by contacting the 1,2-saturated steroid with *A. simplex* or *Bacillis cyclooxydans* in the presence of exogenous electron carrier and a water-immiscible aromatic hydrocarbon solvent.

U.S. Pat. No. 4,749,649 discloses the use of scavengers of toxic oxygen species in the microbial $\Delta^1$-dehydrogenation of steroids.

The microbial enzymatic 11β-hydroxylation of steroids with microorganisms such as *Curvularia lunata* is known to those skilled in the art, see for example U.S. Pat. No. 3,419,470. The concentration of the substrate undergoing 11-β hydroxylation is quite low. For example, U.S. Pat. No. 3,530,038 discloses a maximum concentration of steroid substrates 17α-acetoxypregn-4-en-21-ol-3,20-dione and 17α,21-diacetoxypregn-4-ene-3,20-dione is 0.5 g/L. European Patent EP 0 042 451 A1 again discloses that the amount of steroid substrate concentration does not exceed 0.5 g/L. U.S. Pat. No. 4,353,985 does not give specific examples, and uses 17α,21-orthoesters. U.S. Pat. No. 4,588,683 discloses that the steroid substrate concentration of 17α,20β,21-trihydroxypregn-4-en-3-one is 0.5 g/L. U.S. Pat. No. 4,898,693 discloses that the steroid substrate concentration of 6α-fluoro-17α-hydroxy-16α-methylpregn-4-en-3,20-dione is 0.4 g/L. All but the last patent listed above relate to eliminating unwanted 14α-hydroxylation resulting in high yields of 11β-hydroxylated product (80–92%). However, the substrate charge to the fermentation does not exceed 0.5 g/L. Japanese Published Application 62–118898 discloses the use of *C. lunata* MCI1690 (registered at Microbial Industry Institute strain No. 8515) at a substrate concentration of 10 g/L but with substance S and analogs thereof, not the substrate of the present invention. The process of the present invention uses a different culture than that of the Japanese 62–118898 and provides high yields using high substrate concentrations.

The functionalization of the $C_{21}$-methyl group of pregnanes followed by displacement with acetate to produce the corresponding 21-acetate is known to those skilled in the art. GB 2,318,790 discloses the transformation of the $C_{21}$-methyl group of a $\Delta^{1-11}$β-hydroxy steroid to the corresponding 21-hydroxy steroid by functionalization with one bromine atom followed by displacement with acetate. The process of the present invention does not use bromine.

GB 2,318,790 discloses the transformation of 17α-hydroxy-6α-methylpregn-4-ene-3,20-dione 17-acetate (I) to 11β,17α-dihydroxy-21-diiodo-6α-methylpregna-1,4-diene-3,20-dione (V) by microbial $\Delta^1$-dehydrogenation by use of *Nocardia simplex*, microbial 11β-hydroxylation by use of *C. lunata* and 21-hydroxylation by use of bromine. The present invention transforms 17α-hydroxy-6α-methylpregn-4-ene-3,20-dione 17-acetate (I) to 11β,17α-dihydroxy-21-diiodo-6α-methylpregna-1,4-diene-3,20-dione (V) but does not use bromine.

SUMMARY OF INVENTION

Disclosed is a process for the preparation of 11β,17α,21-trihydroxy-6α-methylpregna-1,4-diene-3,20-dione 21-acetate (VI) which comprises:

(1) contacting 17α-hydroxy-6α-methylpregn-4-ene-3,20-dione 17-acetate (I) with a $\Delta^1$-dehydrogenase to produce 17α-hydroxy-6α-methylpregna-1,4-diene-3,20-dione 17 acetate (II);

(2) contacting 17α-hydroxy-6α-methylpregna-1,4-diene-3,20-dione 17 acetate (II) with a 11β-hydroxylase to produce 11β,17α-dihydroxy-6α-methylpregna-1,4-diene-3,20-dione 17-acetate (III);

(3) hydrolyzing the 11β,17α-dihydroxy-6α-methylpregna-1,4-diene-3,20-dione 17-acetate (III) to producel 11β,17α-dihydroxy-6α-methylpregna-1,4-diene-3,20-dione (IV);

(4) contacting 11β,17α-dihydroxy-6α-methylpregna-1,4-diene-3,20-dione (IV) with iodine, a catalyst, a mild base to produce 11β,17α-dihydroxy-21-diiodo-6α-methylpregna-1,4-diene-3,20-dione (V) and (5) contacting 11β,17α-dihydroxy-21-diiodo-6α-methylpregna-1,4-diene-3,20-dione (V) with a salt of acetic acid.

Also disclosed is a diiodo steroid of the formula:

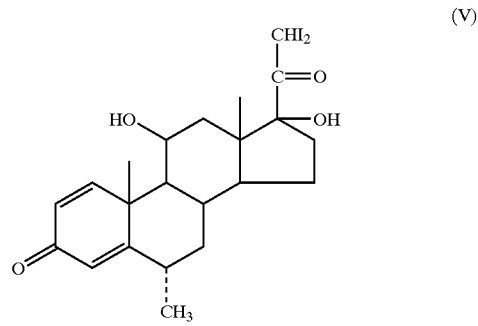

Further disclosed is a process for the removal of residual unhydroxylated material which comprises:

(1) contacting 17α-hydroxy-6α-methylpregn-4-ene-3,20-dione 17-acetate (I) with a $\Delta^1$-dehydrogenase to produce 17α-hydroxy-6α-methylpregna-1,4-diene-3,20-dione 17 acetate (II), (2) crystallizing the 17α-hydroxy-6α-methylpregna-1,4-diene-3,20-dione 17 acetate (II) produced from a nonpolar solvent or solvent mixture.

Additionally disclosed is a process for the purification of 11β,17α-dihydroxy-6α-methylpregna-1,4-diene-3,20-dione 17-acetate (III) produced by a 11β-hydroxylase which comprises:

(1) crystallization from a solvent selected from the group consisting of toluene, benzene, xylene, n-butyl acetate and mixtures thereof with hydrocarbon solvents selected from the group consisting of hexane, heptane, isooctane, cyclohexane and methylcyclohexane.

DETAILED DESCRIPTION OF THE INVENTION

The first two individual steps of the present invention, microbial $\Delta^1$-dehydrogenation with *A. simplex* and 11β-hydroxylation with *C. lunata* are known to those skilled in the art. The chemical transformation of a $C_{21}$-methyl group of a pregnane to the corresponding 21-acetate is also generally known to those skilled in the art. However, the use of the diiodo steroid (V) is novel.

Detailed Description of the $\Delta^1$-Dehydrogenation Step

17α-Hydroxy-6α-methylpregn-4-ene-3,20-dione 17-acetate (I) is dehydrogenated to form 17α-hydroxy-6α-methylpregna-1,4-diene-3,20-dione 17 acetate (II) as set forth below and more specifically as set forth in EXAMPLEs 1–11.

The conversion of 17α-hydroxy-6α-methylpregn-4-ene-3,20-dione 17-acetate (I) to 17α-hydroxy-6α-methylpregna-1,4-diene-3,20-dione 17 acetate (II) can be performed with different enzymatic preparations from *A. simplex*. The enzymatic preparation can be in the form of an actively growing culture, a whole cell concentrate, a cell free extract or as immobilized cells. Preferably, whole cell concentrates are used.

In a two-phase system, it is preferred to use whole cell concentrates. The non-aqueous phase contains 17α-hydroxy-6α-methylpregn-4-ene-3,20-dione 17-acetate (I), an exogenous electron carrier and a water-immiscible organic solvent. Operable exogenous electron acceptors are selected from the group consisting of menadione, menadione bisulfilte, 1,4-naphthoquinone, phenazine methosulfate, phenazine ethosulfate and vitamin K-type compounds. It is preferred that the exogenous electron carrier is selected from the group consisting of menadione and 1,4-naphthoquinone; it is more preferred that the exogenous electron carrier is menadione. The exogenous electron carrier is added in catalytic amounts, for example, in an amount of from about 4 to about 6% (wt exogenous electron carrier/wt of 17α-hydroxy-6α-methylpregn-4-ene-3,20-dione 17-acetate (I)). It is more preferred that the exogenous electron carrier is present in an amount of about 5%. Operable water-immiscible organic solvents are selected from the group consisting of toluene, xylene, benzene, heptane, methylene chloride, n-octanol, carbon tetrachloride and higher n-alcohols or mixtures thereof. It is preferred that the water-immiscible organic solvent be a mixture of methylene chloride and toluene. It is preferred that the water-immiscible organic solvent be present in a range of from about 1 to about 99%; it is more preferred that the water-immiscible organic solvent is present in a range of from about 60 to about 95%.

It is preferred that the 17α-hydroxy-6α-methylpregn-4-ene-3,20-dione 17-acetate (I) be present in a concentration of from about 10 g/L to about 125 g/L; it is more preferred that the 17α-hydroxy-6α-methylpregn-4-ene-3,20-dione 17-acetate (I) is present in a concentration from about 50 g/L to about 100 g/L.

The aqueous phase is prepared by mixing catalase, water, and a cell concentrate of *A. simplex*. It is preferred that the aqueous phase contains catalase.

The aqueous phase is added while stirring to begin the bioconversion. The temperature is controlled at about 30° and the pH is controlled between 8.7 and 8.9 by the addition of base, preferably hydroxide, and more preferably sodium hydroxide. The reaction mixture is preferably sparged with both air (1 part) and nitrogen (2 parts) and permitted to react until less than about 1% residual 17α-hydroxy-6α-methylpregn-4-ene-3,20-dione 17-acetate (I) remains. If necessary, additional source of enzyme is added to assure completion of the reaction.

When the reaction is complete, the pH control, the air and nitrogen feeds, and agitation are turned off. The phases are then separated and additional water-immiscible organic solvent can be used to re-extract the aqueous phase for additional recovery. Again the agitation is stopped and the aqueous phase is permitted to partition. The water-immiscible organic solvent phase is drained from the reactor and the spent aqueous cell layer is discarded. The water-immiscible organic solvent phase is filtered to assure cell removal. The clarified filtrate is then concentrated and the desired 17α-hydroxy-6α-methylpregna-1,4-diene-3,20-dione 17 acetate (II) is isolated by means well known to those skilled in the art.

Detailed Description of the 11β-Hydroxylation Step

17α-hydroxy-6α-methylpregna-1,4-diene-3,20-dione 17 acetate (II) is hydroxylated to form 11β,17α-dihydroxy-6α-methylpregna-1,4-diene-3,20-dione 17 acetate (III) as is known to those skilled in the art and more specifically as set forth below and more specifically as set forth in EXAMPLEs 12–14.

17α-hydroxy-6α-methylpregna-1,4-diene-3,20-dione 17 acetate (II) is microbiologically hydroxylated at the 11-position to produce 11β,17α-dihydroxy-6α-methylpregna-1,4-diene-3,20-dione 17 acetate (III). Any filamentous fungi belonging to the genus *Curvularia* (*Cochliobolus, Pseudocochliobolus*, teleomorphs) capable of 11β-hydroxylating 17α-hydroxy-6α-methylpregna-1,4-diene-3,20-dione 17 acetate (II) can be used in the invention process. Preferably, *Curvularia lunata* (*Cochliobolus lunatus, Pseudochocliobolus lunatus*, teleomorphs) is used. More preferably, *Curvularia lunata* NRRL 2380 (ATCC 12017) is used.

The fungal hydroxylase may be utilized in the form of an actively growing culture, a whole-cell concentrate, or a cell-free extract. Preferably the fungus is grown in submerged culture under aerobic conditions, using any art-recognized procedure, and the 11β-hydroxylation reaction performed in situ.

The desired fungus may be cultured under conditions identified in EXAMPLEs 12–14 using the ingredients specified, or other suitable carbon and nitrogen sources as is known to those skilled in the art. Generally a primary and secondary vegetative seed procedure is used in preparation for the fungal steroid-hydroxylation. Alternatively, a primary vegetative seed can be used directly to inoculate bioconversion media.

Primary vegetative seed cultures may be incubated for a period of about 24 to about 72 hours (preferably about 48 hours) at a temperature between about 22° and about 37° (preferably about 28°), and a pH between about 3.0 and about 7.5. Secondary vegetative seed medium is inoculated with about 0.006% to about 0.1% (v/v) primary vegetative seed culture, but typically about 0.012% (v/v), and incubated for a period of about 36 to about 72 hours (preferably about 48 to about 65 hours) at a temperature between about 22° and about 37° (preferably about 28°). The pH of the secondary seed medium can be between about 2.5 and about 5.0, but preferably between about 3.0 and about 4.0. The bioconversion medium, which can be the same or similar to the secondary vegetative seed medium, is inoculated with about 1% to about 10% (v/v) secondary vegetative seed culture, but typically about 3% (v/v). Bioconversion fermentation conditions can be the same as those used for cultivation of the secondary vegetative seed culture. After an initial incubation period of about 9 to about 72 hours (preferably about 18 to about 24 hours), 17α-hydroxy-6α-methylpregna-1,4-diene-3,20-dione 17 acetate (II), preferably micronized, is added to the bioconversion culture. The micronized 17α-hydroxy-6α-methylpregna-1,4-diene-3,20-dione 17 acetate (II) can be added as a dry powder or aqueous slurry, either as a single addition, a series of additions, or a continual feed. It is preferred to use the micronized 17α-hydroxy-6α-methylpregna-1,4-diene-3,20-dione 17 acetate (II) substrate at a concentration of greater than 1 g/L, more preferably greater than 2.5 g/L, even more preferably greater than 5 g/L. Bioconversion of 17α-hydroxy-6α-methylpregna-1,4-diene-3,20-dione 17 acetate (II) to 11β,17α-dihydroxy-6α-methylpregna-1,4-diene-3,20-dione 17 acetate (III) is allowed to proceed for between about 6 and about 12 days, but typically about 9 to about 10 days.

The rate, and extent, of 11β-hydroxylation can be greatly improved by: (i) culturing the selected fungus, and performing the bioconversion, in the presence of a detergent. The detergent may be selected from the group consisting of non-ionic detergents, but preferably the sub-group consisting of ethoxylated alkyl phenols. More preferably, octylphenoxy polyethoxy ethanol is used; (ii) culturing the selected fungus, and performing the bioconversion, in the presence of a natural oil. The natural oil may be selected from, but not restricted to, the group consisting of caster oil, corn oil, cottonseed oil, lard oil, linseed oil, olive oil, peanut oil, rapeseed oil, safflower seed oil, soybean oil, sunflower seed oil, and wheat germ oil. Preferably, soybean oil is used; (iii) using a timed nitrate addition. The source of nitrate may be selected from, but not restricted to, the group consisting of ammonium nitrate, calcium nitrate, and sodium nitrate. Preferably, ammonium nitrate is used. Nitrate can be added any time after substrate addition, but preferably between about 17 and about 24 hours post-substrate addition; (iv) using a timed temperature shift from about 28° to about 37°. Temperature shifting can be performed any time after substrate addition, but preferably between about 17 to about 24 hours post-substrate addition; (v) using any combination of the methodologies identified in (i)–(iv).

Once the bioconversion of 17α-hydroxy-6α-methylpregna-1,4-diene-3,20-dione 17 acetate (II) to 11β,17α-dihydroxy-6α-methylpregna-1,4-diene-3,20-dione 17 acetate (III) is complete, 11β,17α-dihydroxy-6α-methylpregna-1,4-diene-3,20-dione 17 acetate (III) can be isolated using any one of a number of art-recognized procedures. Preferably, the whole beer is extracted with a water-immiscible organic solvent, such as ethyl acetate or butyl acetate, and the 11β,17α-dihydroxy-6α-methylpregna-1,4-diene-3,20-dione 17 acetate (III) isolated by crystallization.

The crude 11β-hydroxylated intermediate, 11β,17α-dihydroxy-6α-methylpregna-1,4-diene-3,20-dione 17 acetate (III), is purified by crystallization from a nonpolar solvent or solvent mixture. It is preferred that the crystallization solvents include a solvent selected from the group consisting of toluene, benzene, xylene, n-butyl acetate and mixtures thereof with hydrocarbon solvents selected from the group consisting of hexane, heptane, isooctane, cyclohexane and methylcyclohexane. The preferred crystallization solvent is a mixture of toluene/isooctane (1/1). The crystallization is performed at temperatures as low as about –40° or as high as about +25°. The preferred crystallization temperature is about 0°.

Detailed Description of the 21-Acetate Formation Step

The purified 11β,17α-dihydroxy-6α-methylpregna-1,4-diene-3,20-dione 17 acetate (III) is then deacetylated to give the corresponding 11β,17α-dihydroxy-6α-methylpregna-1,4-diene-3,20-dione (IV). The deacylation or hydrolyzing is accomplished by treatment with a base selected from the group consisting of carbonate, hydroxide or $C_1$–$C_4$ alkoxide. It is preferred that the base is selected from the group consisting of carbonate in methanol, hydroxide in aqueous methanol or methoxide. It is more preferred that the base is methoxide. The preferred method is to treat the substrate with sodium methoxide in methanol at about 25°. Ethanol, isopropanol, n-propanol, and other lower alcohols are also operable solvents. Alkoxide salts of other electropositive elements such as potassium, lithium, magnesium, calcium, titanium, aluminum are also operable. The reaction is carried out at temperatures as low as about –40° or as high as about +65°. The preferred temperature range is about 0° to about 25°. The most preferred temperature is about 25° because the reaction is complete in less than 3 hrs. at this temperature.

The 11β,17α-dihydroxy-6α-methylpregna-1,4-diene-3,20-dione (IV) is then 21-acetoxylated to give the desired 11β,17α,21-trihydroxy-6α-methylpregna-1,4-diene-3,20-dione 17-acetate (VI). This 21-acetoxylation is effected by treatment with iodine, a catalyst such as calcium bromide, and a mild base such as calcium hydroxide. It is preferred to use a mixture of calcium oxide, calcium hydroxide, and calcium bromide in methanol. The process is operable with about 1.5–2.5 equivalents of iodine and about 1.0–10 equivalents of calcium hydroxide and/or oxide. The process is operable with as little as 0.05 equivalents of calcium bromide. It is preferred to use 2.0 equivalents of iodine, 1.2 equivalents of calcium oxide, 3.75 eqivalents of calcium hydroxide, and 0.7 equivalents of calcium bromide. It is important to add the iodine more slowly than it is consumed to avoid over-iodination which gives rise to 17β-carbomethoxy-6α-methyl-11β,17α-dihydroxyandrosta-1,4-dien-3-one. The reaction temperature should be greater than +10°, preferably greater than +25°, most preferably +25° during the addition of the first half of the iodine in order to avoid formation of 17β-carbomethoxy-6α-methyl-11β,17α-dihydroxyandrosta-1,4-dien-3-one. The reaction temperature should be below +40°, preferably below +25°, most preferably at 0° during the second half of the iodine add in order to minimize degradation of the product diiodide.

The 11β,17α-dihydroxy-21-diiodo-6α-methylpregna-1,4-diene-3,20-dione (V) is finally contacted with a salt of acetic acid, preferably triethylammonium or potassium acetate. However, sodium, magnesium and other metal or amine salt of acetic acid is operable.

DEFINITIONS

The definitions and explanations below are for the terms as used throughout this entire document including both the specification and the claims.

All temperatures are in degrees Celsius.

RPM refers to revolutions per minute.

SCFM refers to standard cubic feet per minute.

TLC refers to thin-layer chromatography.

HPLC refers to high pressure liquid chromatography.

psig refers to pounds per square inch gage.

DO refers to dissolved oxygen.

RO refers to reverse osmosis.

SLM refers to standard liters per minute.

VVM refers to volume per minute.

OUR refers to oxygen uptake rate.

DDQ refers to 2,3-dichloro-5,6-dicyano-1,4-benzoquinone.

Chromatography (column and flash chromatography) refers to purification/separation of compounds expressed as (support, eluent). It is understood that the appropriate fractions are pooled and concentrated to give the desired compound(s).

Pharmaceutically acceptable refers to those properties and/or substances which are acceptable to the patient from a pharmacological/toxicological point of view and to the manufacturing pharmaceutical chemist from a physical/chemical point of view regarding composition, formulation, stability, patient acceptance and bioavailability.

When solvent pairs are used, the ratios of solvents used are volume/volume (v/v).

When the solubility of a solid in a solvent is used the ratio of the solid to the solvent is weight/volume (wt/v).

EXAMPLES

Without further elaboration, it is believed that one skilled in the art can, using the preceding description, practice the present invention to its fullest extent. The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques.

Example 1

Bioconversion of 17α-hydroxy-6α-methylpregn-4-ene-3,20-dione 17-acetate (I) to 17α-hydroxy-6α-methylpregna-1,4-diene-3,20-dione 17 acetate (II)

17α-Hydroxy-6α-methylpregn-4-ene-3,20-dione 17-acetate (I, 500 g) and menadione (10 g) are mixed with toluene (2200 mL) and methylene chloride (2300 mL). The aqueous phase is prepared as a mixture of catalase (0.25 g), *A. simplex* cell concentrate (obtained by fermentation, concentrated to contain about 20% dried solids, 1000 mL) and water (1000 mL). The aqueous phase is added to the briskly agitated toluene mixture (360 RPM) to begin the bioconversion. The temperature is controlled a 30° using a water bath and the pH is controlled between 8.7 and 8.9 using sodium hydroxide (2N) additions. The reaction mixture is sparged with a regulated flow of air (0.3 SCFH) and nitrogen (0.6 SCFM), respectively.

The mixture is allowed to react until less than 1% residual starting material (I) remains. If necessary, more *A. simplex* cells are added during the reaction to assure completion.

When the reaction is complete, the pH control, air feed, nitrogen feed, and agitation are turned off and the aqueous phase is permitted to float. The toluene/methylene chloride mixture is drawn from the bottom of the reactor. Additional methylene chloride (3000 mL) is added to the bioconversion vessel and the agitator is started to further extract the aqueous layer. The agitation is stopped and the aqueous phase is allowed to rise. The lean methylene chloride extract is drained from the reactor and the spent aqueous cell layer is discarded.

The rich and lean extracts are filtered. The clarified filtrate is then concentrated to a thick slurry. The solids are collected by filtration, washed with branched octane (450 mL) and dried in a vacuum oven at 50° to give the title compound (II).

Examples 2–11

Bioconversion of 17α-hydroxy-6α-methylpregn-4-ene-3,20-dione 17-acetate (I) to 17α-hydroxy-6α-methylpregna-1,4-diene-3,20-dione 17 acetate (II)

Following the general procedure of EXAMPLE 1, and making non-critical variations but altering the amount of cells, water and reaction as set forth below, the title compound (II) is obtained.

| EXAMPLE | SUBSTRATE (g) | CELLS (mL) | WATER (mL) | REACTION TIME (hrs) |
| --- | --- | --- | --- | --- |
| 2 | 500 | 1000 | 0 | 161 |
| 3 | 500 | 1000 | 0 | 162 |
| 4 | 500 | 1000 | 500 | 95 |
| 5 | 500 | 1000 | 1000 | 97 |
| 6 | 500 | 750 | 1250 | 146 |
| 7 | 500 | 1000 | 1000 | 97 |
| 8 | 500 | 1000 | 1000 | 125 |
| 9 | 500 | 1000 | 1000 | 120 |
| 10 | 500 | 1000 | 1000 | 120 |
| 11 | 500 | 1000 | 1000 | 117 |

Example 12

Bioconversion of 17α-hydroxy-6α-methylpregna-1,4-diene-3,20-dione 17 acetate (II) To 11β,17α-dihydroxy-6α-methylpregna-1,4-diene-3,20-dione 17-acetate (III)

The bioconversion of 17α-hydroxy-6α-methylpregna-1,4-diene-3,20-dione 17 acetate (II) to 11β,17α-dihydroxy-6α-methylpregna-1,4-diene-3,20-dione 17-acetate (III) is performed using a submerged culture of *Curvularia lunata* NRRL 2380 (ATCC 12017) at a 10 L scale.

(A) Primary-Seed Stage

Frozen vegetative cells of *C. lunata* NRRL 2380 are thawed, transferred to potato-dextrose-agar plates (PDA), and incubated at 28° for 72 hours. Single mycelial-plugs (6–7 mm diam.) are used to inoculate siliconized 500 mL stippled shake flasks containing 100 mL primary-seed medium. Primary-seed medium consists of (per liter of reverse osmosis water): dextrin, 50 g; soyflour, 35 g; cerelose, 5 g; coboalt chloride hexahydrate, 2 mg; silicone defoamer (SAG 471), 0.5 mL; pre-sterilization pH 7.0–7.2, adjusted with sodium hydroxude (2N). *Curvularia lunata* NRRL 2380 is incubated for 48 hours at 280, using a controlled-environment incubator-shaker set at 280 rpm. (1" orbital stroke).

(B) Secondary-Seed Stage

Ten-liter secondary-seed fermentations are inoculated using vegetative primary-seed culture (1.2 mL; 0.012% [v/v]

inoculation rate). Secondary-seed medium contains (per liter of reverse osmosis water): anhydrous glucose (20 g), soyflour (20 g), soybean oil (30 mL); octylphenoxy polyethoxy ethanol (0.25 mL), riboflavin (10 mg), silicone defoamer (SAG 471, 0.5 mL); mangnesium hepahydrate (1 g), potassium dihydrogen phosphate (0.74 g), pre-sterilization pH=2.95–3.00, and the pH is adjusted with concentrated sulfuric acid. The fermentors, containing secondary-seed medium, are sterilized for 20 minutes at 121° using both jacket and injection steam. The agitation rate during sterilization is 200 rpm. Post-sterilization, the medium pH is adjusted to 3.0 using sterile sulfuric acid (5%). *Curvularia lunata* NRRL 2380 is incubated at 28° using the following initial parameters: agitation, 100 rpm.; back pressure=5 psig; air flow=2.5 SLM (0.25 VVM); low dissolved oxygen (DO) set-point, 30%; pH control, none. When the DO first drops to 30%, the air flow is increased to 5 SLM (0.5 VVM). When the culture reachs low DO again, 30% DO is maintained using agitation control. Once a notable drop in the oxygen uptake rate (OUR) of the cultures is observed (generally a drop from 12–14 to 8–9 mmol/L/hr), as they deplete of glucose, secondary-seed cultures are harvested five hours later (approximately 60–65 hours post-inoculation).

(C) Steroid Bioconversion

Ten-liter steroid-bioconversion fermentations are inoculated using 300 mL vegetative secondary-seed culture (3.0% inoculation rate). Steroid-bioconversion medium is essentially the same as secondary-seed medium, with the exception that octylphenoxy polyethoxy ethanol is increased from 0.25 mL/L to 2.5 mL/L and the anhydrous glucose decreased from 20 g/L to 15 g/L. Sterilization conditions and pH adjustment are as described for secondary-seed medium. *Curvularia lunata* NRRL 2380 is incubated at 28° using essentially the same initial parameters as those used for secondary-seed cultivation, with the exception that the initial agitation rate is increased from 100 rpm to 200 rpm. When the DO first drops to 30%, the air flow is increased from 2.5 SLM (0.25 VVM) to 5 SLM (0.5 VVM). After this initial air-flow change, once the DO reaches 30% again, micronized 17α-hydroxy-6α-methylpregna-1,4-diene-3,20-dione 17 acetate (II, 80 g) is slurried in octylphenoxy polyethoxy ethanol (0.2%, 500 mL) and added to the fermentation. At this point the OUR of the culture would normally be in the 9.5–10.5 mmol/L/h range (generally 18–24 hours post-inoculation). When the OUR of the culture drops to between 6.5–6.0 mmol/L/h (generally 17–18 hours post-substrate addition), ammonium nitrate (7.2 g) is dissolved in RO water (50 mL) is added to the fermentation and the incubation temperature, increased gradually from 28° to 37° (2° every 15 minutes). After the initial air-flow change, agitation control, up to a maximum of 550 rpm, is used throughout the fermentation to maintain DO at 30%. Once maximum agitation is attained, back pressure, in 2 psig increments, is used to maintain DO. Bioconversion is complete in 9–10 days with fermentation beer containing 68–70 g of the title compound 11β,17α-dihydroxy-6α-methylpregna-1,4-diene-3,20-dione 17-acetate (III). Bioconversion cultures are assayed on a daily basis for 11β,17α-dihydroxy-6α-methylpregna-1,4-diene-3,20-dione 17-acetate (III) using HPLC.

Whole-culture extractions are performed using two volumes of warm acetone, with constant shaking for one hour. Cells are separated from the aqueous-acetone mixture by centrifugation (3,000× g for 10 minutes), and an aliquot dried under nitrogen. Steroid extracts are re-dissolved in an appropriate volume of methanol, containing 17α-hydroxy-6α-methylpregna-1,4-dien-3,20-dione 17-acetate as an internal standard. Conditions for HPLC are as follows: Spectra-Physics chromatograph fitted with a C18 reverse-phase column (150×4.6 mm) column; column temperature, 30°; mobile phase, methanol/acetonitrile/0.25% phosphoric acid (10/60/30, v/v/v); flow rate=1 mL/minute; detection, 240 nm; run time=10 minutes.

(D) Isolation Procedure

The whole beer at harvest is mixed well. A flocculent is added to the broth and the rich solids are recovered by centrifugation. The rich solids are extracted with butyl acetate and the rich extract is recovered by centrifugation. The extract is polished and concentrated by distillation to a specific volume and cooled to crystallize the product. The crystal slurry is filtered and the mother liquor is saved to isolate second crop crystals. The wet crystals are re-dissolved in hot butyl acetate and the mixture is concentrated to saturation then cooled to crystallize the product. The crystal slurry is filtered and the cake is washed with branched octane and dried. The product may be re-crystallized in butyl acetate or toluene to upgrade quality.

The rich solids can also be extracted with acetone. The acetone slurry is centrifuged to remove cell mass. The rich acetone extract is polished and concentrated by vacuum distillation to an aqueous slurry. The slurry is then extracted with butyl acetate and the organic extract is polished, concentrated by vacuum distillation to a specific volume, and cooled to crystallize the product. The crystal slurry is filtered and the mother liquor is saved to isolate second crop crystals. The wet crystals are re-dissolved in hot butyl acetate and the solution is concentrated to saturation then cooled to crystallize the product. The crystal slurry is filtered and the cake is washed with branched octane and dried. The product may be re-crystallized with butyl acetate or toluene to upgrade quality.

Example 13

Bioconversion of 17α-hydroxy-6α-methylpregna-1,4-diene-3,20-dione 17 acetate (II) To 11β,17α-dihydroxy-6α-methylpregna-1,4-diene-3,20-dione 17-acetate (III)

Following the general procedure of EXAMPLE 12 and making non-critical variations but using 17α-hydroxy-6α-methylpregna-1,4-diene-3,20-dione 17 acetate (II) at a substrate concentration of about 6 g/L, the title compound is obtained.

Example 14

Bioconversion of 17α-hydroxy-6α-methylpregna-1,4-diene-3,20-dione 17 acetate (II) to 11β,17α-dihydroxy-6α-methylpregna-1,4-diene-3,20-dione 17-acetate (III)

The bioconversion of 17α-hydroxy-6α-methylpregna-1,4-diene-3,20-dione 17 acetate (II) to 11β,17α-dihydroxy-6α-methylpregna-1,4-diene-3,20-dione 17-acetate (III) is performed using a submerged culture of *Curvularia lunata* NRRL 2380 (ATCC 12017) at a shake-flask scale.

(A) Primary-Seed Stage

Seed medium and incubation conditions for *C. lunata* NRRL 2380 are as described in EXAMPLE 12.

(B) Secondary-Seed Stage

One hundred milliliter secondary-seed medium, in a siliconized 500 mL stippled shake flask, is inoculated using one drop of vegetative primary-seed culture. Secondary-seed medium contains (per liter of reverse osmosis water): cerelose, 20 g; dextrin, 50 g; soyflour, 35 g; soybean oil, 30 mL, octylphenoxy polyethoxy ethanol, 0.25 mL; silicone defoamer (SAG 471), 0.5 mL; pre-sterilization pH=2.95–3.00, adjusted with concentrated sulfuric acid. *Curvularia lunata* NRRL 2380 is incubated for 48–50 hours at 28°, using a controlled-environment incubator-shaker set at 275 rpm. (2" orbital stroke).

(C) Steroid Bioconversion

One hundred milliliter steroid-bioconversion medium, in a siliconized 500 mL stippled shake flask, is inoculated using 3 mL vegetative secondary-seed culture (3.0% inoculation rate). Steroid-bioconversion medium is essentially the same as the secondary-seed medium, with the exception that octylphenoxy polyethoxy ethanol is increased from 0.25 mL/L to 2.5 mL/L and pre-sterilization pH is adjusted to 3.95–4.00 with concentrated sulfuric acid. *Curvularia lunata* NRRL 2380 is initially incubated at 28° using essentially the same parameters as those used for secondary-seed cultivation. At approximately 17–18 hours post-inoculation, 1 g micronized 17α-hydroxy-6α-methylpregna-1,4-diene-3, 20-dione 17 acetate (II) is added to the fermentation as a dry powder. At approximately 22–24 hours post-substrate addition, 0.5 mL ammonium nitrate solution (7.2 g per 50 mL reverse osmosis water) is added to the fermentation and the culture further incubated at 37° with shaking (275 rpm, 2" orbital stroke). Bioconversion is complete in 8–11 days with fermentation beer containing about 0.90 g 11β,17α-dihydroxy-6α-methylpregna- 1,4-diene-3,20-dione 17-acetate (III). Bioconversion cultures are periodically assayed for 11β,17α-dihydroxy-6α-methylpregna-1,4-diene-3,20-dione 17-acetate (III) following the procedure described in EXAMPLE 12.

Example 15

Transformation of 11β,17α-dihydroxy-6α-methylpregna-1,4-diene-3,20-dione 17-acetate (III) to 11β,17α-dihydroxy-6α-methylpregna-1,4-diene-3,20-dione (IV)

Sodium methoxide (1.4175 g, 26.2403 mM, 1.05 eq.) in methanol (25%, 6.0 ml) is added to a mixture of 11β,17α-dihydroxy-6α-methylpregna-1,4-diene-3,20-dione 17-acetate (III, EXAMPLE 12, 9.9961 g, 24.9578 mM) in methylene chloride (24 ml) and methanol (10 ml) methanol. The mixture is stirred at 20–25° for 2 hours. The reaction is then quenched with acetic acid (1.6 ml, 1.678 g, 27.95 mM, 1.12 eq.), diluted with water/methanol (1/1; 40 ml), stirred at 20–25° for 1 hr., then diluted with water (100 ml) and concentrated under reduced pressure. The residue is diluted with methanol (20 ml) and water (40 ml), concentrated under reduced pressure and the slurry filtered. The cake is washed with water (20 ml) and dried by a nitrogen stream to give the title compound.

Example 16

Transformation of 11β,17α-dihydroxy-6α-methylpregna-1,4-diene-3,20-dione (IV) to 11β, 17α-dihydroxy-21-diiodo-6α-methylpregna-1,4-diene-3,20-dione (V)

A slurry of 11β,17α-dihydroxy-6α-methylpregna-1,4-diene-3,20-dione (IV, EXAMPLE 15, 30.0050 g, 83.7006 mM), calcium oxide (5.7275 g, 102.13 mM, 1.22 eq.), calcium hydroxide (23.2488 g, 313.79 mM, 3.75 eq.) and calcium bromide (0.5786 g, 2.8946 mM, 0.035 eq.) in methanol (117) at 25° ias treated with a mixture of iodine (42.5052 g, 167.47 mM, 2.00 eq.) and calcium bromide (10.897 g, 54.51 mM, 0.65 eq.) in methanol (120 ml) at a steady rate over 4 hours. The reaction mixture is cooled to 0° halfway through the add. The reaction mixture is then poured into a solution of acetic acid (90 ml) in water (2.25 L). The resulting slurry is filtered and the cake is dried by a nitrogen stream to give the title compound.

Example 17

Transformation of 11β,17α-dihydroxy-21-diiodo-6α-methylpregna-1,4-diene-3,20-dione (V) To 11β, 17α,21 -trihydroxy-6α-methylpregna-1,4-diene-3, 20-dione 17-acetate (VI)

11β,17α-dihydroxy-21-diiodo-6α-methylpregna-1,4-diene-3,20-dione (V, EXAMPLE 16, 45.0033 g, 73.7433 mM) is added to a mixture of acetic acid (110 ml, 115.4 g, 1.922 moles, 26.1 eq.) and triethylamine (167 ml, 121.2 g, 1.198 moles, 16.2 eq.) in 610 ml acetone. The resulting mixture is stirred at 45° for 2 hrs., then cooled to 20–25° and concentrated under reduced pressure. The residue is taken up in methylene chloride (500 ml), washed with aqueous hydrochloric acid (5%, 180 ml) followed by saturated sodium bicarbonate (300 ml) followed by water (340 ml), then filtered through a pad of cartridge grade magnesol (91.72 g), eluting with methylene chloride (1.2 L) followed by acetone/methylene chloride (5/95; 400 ml). The combined eluate is concentrated under reduced pressure to about 400 ml, diluted with methanol (150 ml), and concentrated to about 300 ml. More methanol (150 ml) is added and the mixture is concentrated to about 250 ml. More methanol (100 ml) is added and the mixture is further concentrated, whereupon the product crystallized. The slurry is cooled to −19°, stirred for 2 hrs., then filtered. The cake is washed with methanol/water (1/1; 3×20 ml) and dried by a nitrogen stream to give the title compound. A portion of the above solids (3.994 g) is dissolved in methylene chloride/methanol (2/1; 40 ml), concentrated under reduced pressure to about 30 ml, diluted with methanol (10 ml) and concentrated to about 15 ml (2×) to give a slurry which is cooled to −19°, stirred for 2 hrs., and filtered. The cake is washed with methanol/water (1/1, 0°; 2×10 ml) and dried by a nitrogen stream.

Example 18

Crystallization of 11β,17α-dihydroxy-6α-methylpregna-1,4-diene-3,20-dione 17-Acetate (III) To Remove Residual 17α-hydroxy-6α-methylpregna-1,4-diene-3,20-dione 17-Acetate Crude 11β,17α-dihydroxy-6α-methylpregna-1,4-diene-3, 20-dione 17-acetate (III, 0.9195 g of material containing 17α-hydroxy-6α-methylpregna-1,4-diene-3,20-dione 17-acetate (4.13%) is refluxed in toluene (12 ml), then cooled to 0°, diluted with isooctane (12 ml), and filtered. The cake is washed with isooctane (3×3 ml) then dried by a stream of nitrogen to give the title compound containing 17α-hydroxy-6α-methylpregna-1,4-diene-3,20-dione 17-Acetate (1.12%, 0.8774 g) for 99.5% recovery. The filtrate is concentrated to a solid consisting of a 17.76/82.24 mixture of 11β,17α-dihydroxy-6α-methylpregna-1,4-diene-3,20-dione 17-Acetate (III) to remove residual 17α-hydroxy-6α-methylpregna-1,4-diene-3,20-dione 17-acetate.

CHART A
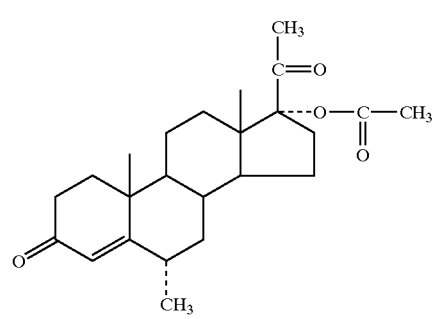
(I)
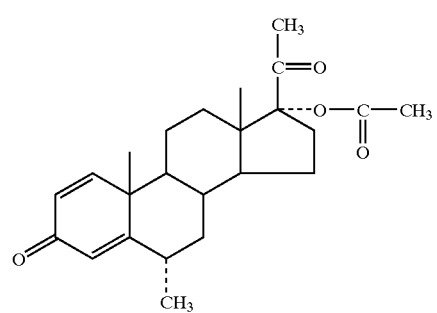
(II)
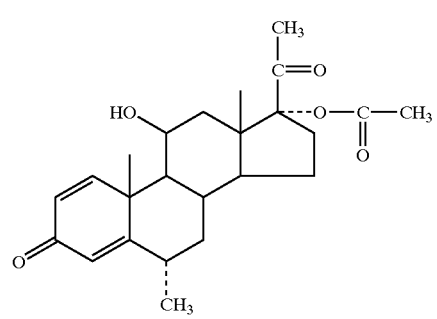
(III)
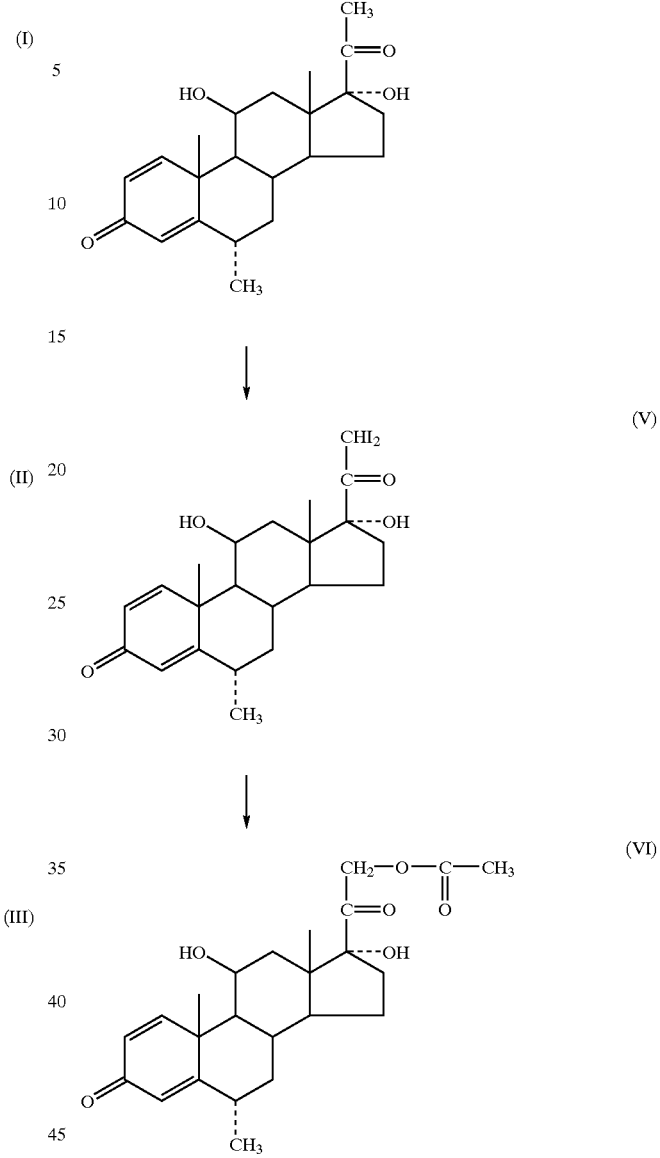
What is claimed is:
1. A process for the preparation of 11β,17α,21-trihydroxy-6α-methylpregna-1,4-diene-3,20-dione 21-acetate (VI) which comprises:
(1) contacting 17α-hydroxy-6α-methylpregn-4-ene-3,20-dione 17-acetate (I) with a Δ¹-dehydrogenase to produce 17α-hydroxy-6α-methylpregna-1,4-diene-3,20-dione 17 acetate (II);

(2) contacting 17α-hydroxy-6α-methylpregna-1,4-diene-3,20-dione 17 acetate (II) with a 11β-hydroxylase to produce 11β,17α-dihydroxy-6α-methylpregna-1,4-diene-3,20-dione 17-acetate (III);

(3) hydrolyzing the 11β,17α-dihydroxy-6α-methylpregna-1,4-diene-3,20-dione 17-acetate (III) to produce 11β,17α-dihydroxy-6α-methylpregna-1,4-diene-3,20-dione (IV);

(4) contacting 11β,17α-dihydroxy-6α-methylpregna-1,4-diene-3,20-dione (IV) with iodine, a catalyst, a mild base to produce 11β,17α-dihydroxy-21-diiodo-6α-methylpregna-1,4-diene-3,20-dione (V) and (5) contacting 11β,17α-dihydroxy-21-diiodo-6α-methylpregna-1,4-diene-3,20-dione (V) with a salt of acetic acid.

2. A process for the preparation of 11β,17α,21-trihydroxy-6α-methylpregna-1,4-diene-3,20-dione 21-acetate (VI) according to claim 1 where the contacting with the $\Delta^1$-dehydrogenase is with $\Delta^1$-dehydrogenase of *A. simplex*.

3. A process for the preparation of 11β,17α,21-trihydroxy-6α-methylpregna-1,4-diene-3,20-dione 21-acetate (VI) according to claim 2 where the $\Delta^1$-dehydrogenase of *A. simplex* is used as fermentation, whole cell concentrate, whole cells, cell free or immobilized cells.

4. A process for the preparation of 11β,17α,21-trihydroxy-6α-methylpregna-1,4-diene-3,20-dione 21-acetate (VI) according to claim 3 where the $\Delta^1$-dehydrogenase of *A. simplex* is used by whole cell concentrate.

5. A process for the preparation of 11β,17α,21-trihydroxy-6α-methylpregna-1,4-diene-3,20-dione 21-acetate (VI) according to claim 2 where the $\Delta^1$-dehydrogenation is conducted in the presence of catalyase.

6. A process for the preparation of 11β,17α,21-trihydroxy-6α-methylpregna-1,4-diene-3,20-dione 21-acetate (VI) according to claim 2 where the $\Delta^1$-dehydrogenation is conducted in the presence of an exogenous electron acceptor.

7. A process for the preparation of 11β,17α,21-trihydroxy-6α-methylpregna-1,4-diene-3,20-dione 21-acetate (VI) according to claim 6 where the exogenous electron acceptor is selected from the group consisting of menadione, menadione bisulfilte, 1,4-naphthoquinone, phenazine methosulfate, phenazine ethosulfate and vitamin K-type compounds.

8. A process for the preparation of 11β,17α,21-trihydroxy-6α-methylpregna-1,4-diene-3,20-dione 21-acetate (VI) according to claim 7 where the exogenous electron acceptor is menadione.

9. A process for the preparation of 11β,17α,21-trihydroxy-6α-methylpregna-1,4-diene-3,20-dione 21-acetate (VI) according to claim 2 where the $\Delta^1$-dehydrogenation is conducted in the presence of water-immiscible organic solvent.

10. A process for the preparation of 11β,17α,21-trihydroxy-6α-methylpregna-1,4-diene-3,20-dione 21-acetate (VI) according to claim 9 where the water-immiscible organic solvent is selected from the group consisting of toluene, xylene, benzene, heptane, methylene chloride, n-octanol, carbon tetrachloride and higher n-alcohols or mixtures thereof.

11. A process for the preparation of 11β,17α,21-trihydroxy-6α-methylpregna-1,4-diene-3,20-dione 21-acetate (VI) according to claim 10 where the water-immiscible organic solvent is a mixture of methylene chloride and toluene.

12. A process for the preparation of 11β,17α,21-trihydroxy-6α-methylpregna-1,4-diene-3,20-dione 21-acetate (VI) according to claim 1 where the 11β-hydroxylase is of *C. lunata*.

13. A process for the preparation of 11β,17α,21-trihydroxy-6α-methylpregna-1,4-diene-3,20-dione 21-acetate (VI) according to claim 12 where the 11β-hydroxylase is of *C. lunata* by fermentation, cell concentrate, whole cells or cell free reaction.

14. A process for the preparation of 11β,17α,21-trihydroxy-6α-methylpregna-1,4-diene-3,20-dione 21-acetate (VI) according to claim 13 where the 11β-hydroxylase is of *C. lunata* by fermentation.

15. A process for the preparation of 11β,17α,21-trihydroxy-6α-methylpregna-1,4-diene-3,20-dione 21-acetate (VI) according to claim 12 where the *C. lunata* is cultured in the presence of a detergent.

16. A process for the preparation of 11β,17α,21-trihydroxy-6α-methylpregna-1,4-diene-3,20-dione 21-acetate (VI) according to claim 15 where the detergent is a non-ionic detergent selected from the group consisting of ethoxylated alcohols, ethoxylated fatty acids, ethoxylated fatty esters and oils, ethoxylated alkyl phenols, polyoxyethylene sorbitan fatty acid esters, polyoxyethylene ethers, polyethylene glycol ethers of alkyl phenols, polyethylene glycol ethers, of primary alcohols and polyethylene glycol ethers of secondary alcohols.

17. A process for the preparation of 11β,17α,21-trihydroxy-6α-methylpregna-1,4-diene-3,20-dione 21-acetate (VI) according to claim 16 where the non-ionic detergent is an ethoxylated alkyl phenol.

18. A process for the preparation of 11β,17α,21-trihydroxy-6α-methylpregna-1,4-diene-3,20-dione 21-acetate (VI) according to claim 17 where the ethoxylated alkyl phenol is octylphenoxy polyethoxy ethanol.

19. A process for the preparation of 11β,17α,21-trihydroxy-6α-methylpregna-1,4-diene-3,20-dione 21-acetate (VI) according to claim 12 where *C. lunata* is cultured in the presence of a natural oil.

20. A process for the preparation of 11β,17α,21-trihydroxy-6α-methylpregna-1,4-diene-3,20-dione 21-acetate (VI) according to claim 19 where the natural oil is selected from the group consisting of soybean oil, castor oil, corn oil, cottonseed oil, lard oil, linseed oil, olive oil, peanut oil, rape seed oil and safflower seed oil.

21. A process for the preparation of 11β,17α,21-trihydroxy-6α-methylpregna-1,4-diene-3,20-dione 21-acetate (VI) according to claim 20 where the natural oil is soybean oil.

22. A process for the preparation of 11β,17α,21-trihydroxy-6α-methylpregna-1,4-diene-3,20-dione 21-acetate (VI) according to claim 12 using a timed nitrate addition.

23. A process for the preparation of 11β,17α,21-trihydroxy-6α-methylpregna-1,4-diene-3,20-dione 21-acetate (VI) according to claim 22 where the source of nitrate is selected from the group consisting of ammonium nitrate, aluminum nitrate, calcium nitrate, sodium nitrate, barium nitrate, potassium nitrate, cupric nitrate, cesium nitrate, magnesium nitrate, manganese nitrate, ferric nitrate, zinc nitrate, cobalt nitrate, lithium nitrate and nitric acid.

24. A process for the preparation of 11β,17α,21-trihydroxy-6α-methylpregna-1,4-diene-3,20-dione 21-acetate (VI) according to claim 23 where the source of nitrate is ammonium nitrate.

25. A process for the preparation of 11β,17α,21-trihydroxy-6α-methylpregna-1,4-diene-3,20-dione 21-acetate (VI) according to claim 12 which uses a temperature shift.

26. A process for the preparation of 11β,17α,21-trihydroxy-6α-methylpregna-1,4-diene-3,20-dione 21-acetate (VI) according to claim 25 where the temperature shift is from about 28° to about 37°.

27. A process for the preparation of 11β,17α,21-trihydroxy-6α-methylpregna-1,4-diene-3,20-dione 21-acetate (VI) according to claim 1 where the hydrolyzing is performed with a base selected from the group consisting of carbonate, hydroxide or $C_1$–$C_4$ alkoxide.

28. A process for the preparation of 11β,17α,21-trihydroxy-6α-methylpregna-1,4-diene-3,20-dione 21-acetate (VI) according to claim 27 where the base is selected from the group consisting of carbonate in methanol, hydroxide in aqueous methanol or methoxide.

29. A process for the preparation of 11β,17α,21-trihydroxy-6α-methylpregna-1,4-diene-3,20-dione 21-acetate (VI) according to claim 28 where the base is methoxide.

30. A process for the preparation of 11β,17α,21-trihydroxy-6α-methylpregna-1,4-diene-3,20-dione 21-acetate (VI) according to claim 27 where more than one equivalent of base is used.

31. A process for the preparation of 11β,17α,21-trihydroxy-6α-methylpregna-1,4-diene-3,20-dione 21-acetate (VI) according to claim 1 where the product of step (3) is contacted with iodine in the presence of base and bromide ion.

32. A process for the preparation of 11β,17α,21-trihydroxy-6α-methylpregna-1,4-diene-3,20-dione 21-acetate (VI) according to claim 31 where the base is selected from the group consisting of hydroxide, $C_1$–$C_4$ alkoxide.

33. A process for the preparation of 11β,17α,21-trihydroxy-6α-methylpregna-1,4-diene-3,20-dione 21-acetate (VI) according to claim 32 where the base is hydroxide.

34. A process for the preparation of 11β,17α,21-trihydroxy-6α-methylpregna-1,4-diene-3,20-dione 21-acetate (VI) according to claim 31 where the bromide is present in a catalytic amount.

35. A process for the preparation of 11β,17α,21-trihydroxy-6α-methylpregna-1,4-diene-3,20-dione 21-acetate (VI) according to claim 1 where the product of step (4) is contacted with $CH_3$—$COO^-$.

36. A process for the preparation of 11β,17α,21-trihydroxy-6α-methylpregna-1,4-diene-3,20-dione 21-acetate (VI) according to claim 1 where the 11β,17α,21-trihydroxy-6α-methylpregna-1,4-diene-3,20-dione 21-acetate (VI) produced contains not more than 0.1% of any impurity.

\* \* \* \* \*